United States Patent [19]

Gilchrist

[11] Patent Number: 5,470,585
[45] Date of Patent: Nov. 28, 1995

[54] MEDICINAL SUBSTANCE FOR TOPICAL APPLICATION

[75] Inventor: Thomas Gilchrist, Ayr, Scotland

[73] Assignee: Giltech Limited, Scotland

[21] Appl. No.: 421,005

[22] Filed: Apr. 12, 1995

Related U.S. Application Data

[63] Continuation of Ser. No. 121,411, Sep. 15, 1993, abandoned, which is a continuation of Ser. No. 688,546, Jun. 10, 1991, abandoned.

[30] Foreign Application Priority Data

Jan. 27, 1989 [GB] United Kingdom ............... 8901846
Feb. 8, 1989 [GB] United Kingdom ............... 8902785
Mar. 2, 1989 [GB] United Kingdom ............... 8904806

[51] Int. Cl.$^6$ .................... A01N 59/16; A01N 59/26; A61F 13/00
[52] U.S. Cl. .................... 424/604; 424/409; 424/411; 424/417; 424/421; 424/443; 424/444; 424/445; 424/446; 424/447; 424/449; 424/489; 424/618; 604/304; 604/305; 604/307; 604/308; 604/890.1
[58] Field of Search .................... 424/604, 409, 424/411, 417, 421, 443, 444, 445, 446, 447, 449, 489, 618, 619; 604/1, 2, 3, 304, 305, 307, 308, 890.1

[56] References Cited

U.S. PATENT DOCUMENTS

| | | | |
|---|---|---|---|
| 2,510,510 | 6/1950 | Mendenhall | 252/107 |
| 3,983,209 | 9/1976 | Schmitt | 424/618 |
| 4,354,490 | 10/1982 | Rogers | 604/403 |
| 4,482,541 | 11/1984 | Telfer et al. | 424/601 |
| 4,559,033 | 12/1985 | Stephen et al. | 604/49 |
| 4,564,361 | 1/1986 | Akiyama | 604/265 |
| 4,849,223 | 7/1989 | Pratt et al. | 424/618 |
| 4,902,503 | 2/1990 | Umemura et al. | 424/618 |
| 4,906,466 | 3/1990 | Edwards et al. | 424/421 |
| 4,919,658 | 4/1990 | Badia | 604/265 |
| 4,933,178 | 6/1990 | Capelli | 424/618 |
| 5,290,544 | 3/1994 | Shimono et al. | 424/618 |
| 5,330,770 | 7/1994 | Kuno | 424/618 |
| 5,413,788 | 5/1995 | Edwards et al. | 424/618 |

FOREIGN PATENT DOCUMENTS

| | | |
|---|---|---|
| 0042219 | 12/1981 | European Pat. Off. . |
| 0059694 | 8/1982 | European Pat. Off. . |
| 0080330 | 6/1983 | European Pat. Off. . |
| 0140538 | 5/1985 | European Pat. Off. . |
| 0335564 | 10/1989 | European Pat. Off. . |
| 2506162 | 11/1982 | France . |
| 3726617 | 7/1988 | Germany . |
| 37201 | 1/1991 | Japan . |
| 1511381 | 5/1978 | United Kingdom . |
| 1565906 | 4/1980 | United Kingdom . |
| 2035290 | 6/1980 | United Kingdom . |
| 2062612 | 5/1981 | United Kingdom . |
| 2077586 | 12/1981 | United Kingdom . |
| 2094256 | 9/1982 | United Kingdom . |
| 2125698 | 3/1983 | United Kingdom . |
| 2150023 | 6/1985 | United Kingdom . |
| 8501210 | 3/1985 | WIPO . |
| 89/01793 | 3/1989 | WIPO . |

OTHER PUBLICATIONS

Smith & Nephew Pharmaceuticals Ltd., (concerning development of Flamazine), 9 pp. date unavailable.
H. Liedberg and T. Lundeberg, "Silver Alloy Coated Catheters Reduce Catheter-associated Bacteriuria", (1990) British Journal of Urology, No. 65, 3 pp.

*Primary Examiner*—Allen J. Robinson
*Assistant Examiner*—John D. Pak
*Attorney, Agent, or Firm*—Ratner & Prestia

[57] ABSTRACT

A medicinal substance for topical application is disclosed. The substance comprises a water-soluble glass containing silver or a silver compound. Typically, the glass comprises phosphorus pentoxide and contains silver oxide. The substance may be used for the treatment of wounds, catheter and tubing entry points, stoma sites and body passage entrances where bacterial growth and migration are rife. The glass may be in the form of a powder, granules, woven into a dressing form, a sinter shaped in a particular way or used as filler in polymers for surface release.

7 Claims, 4 Drawing Sheets

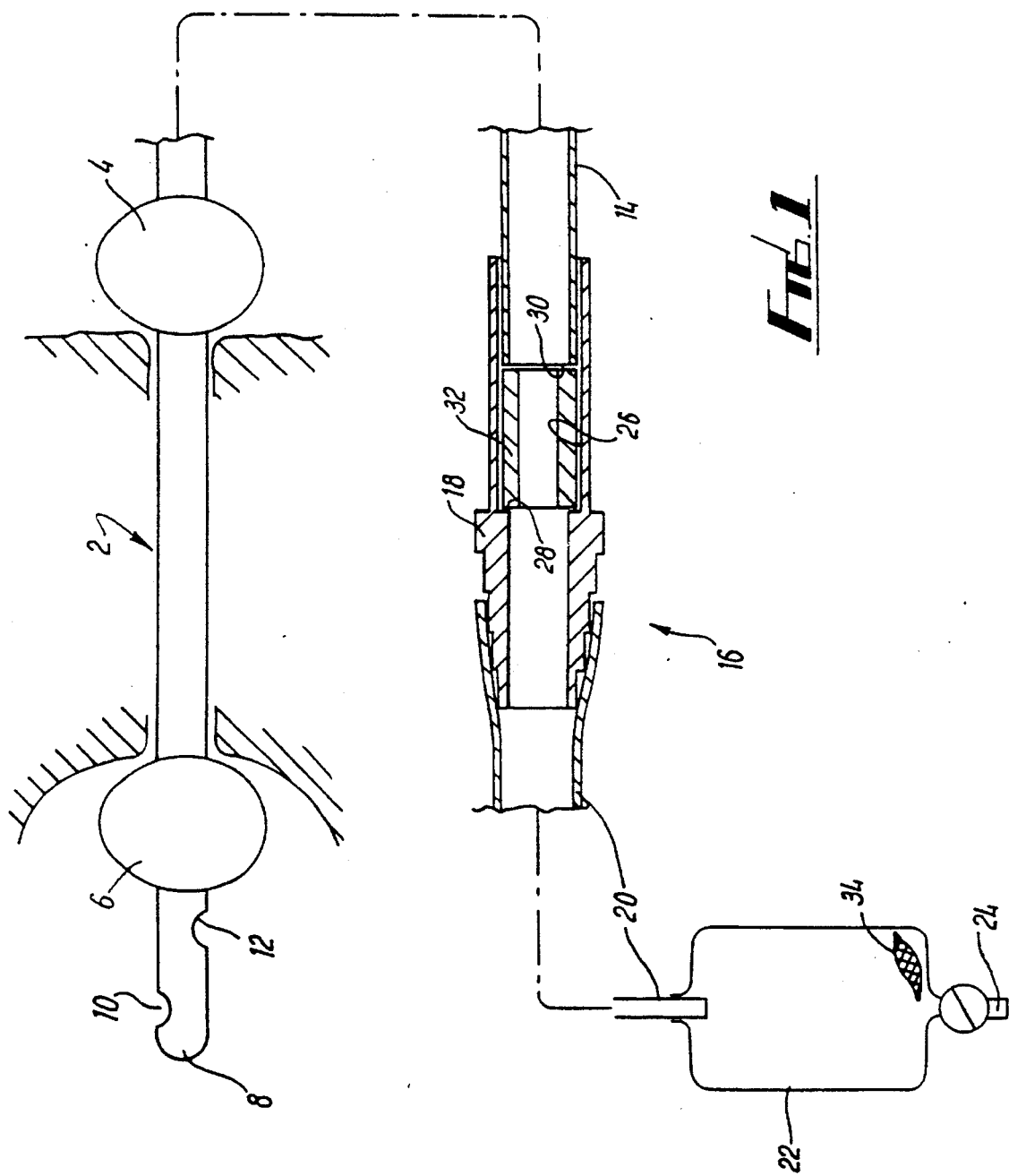

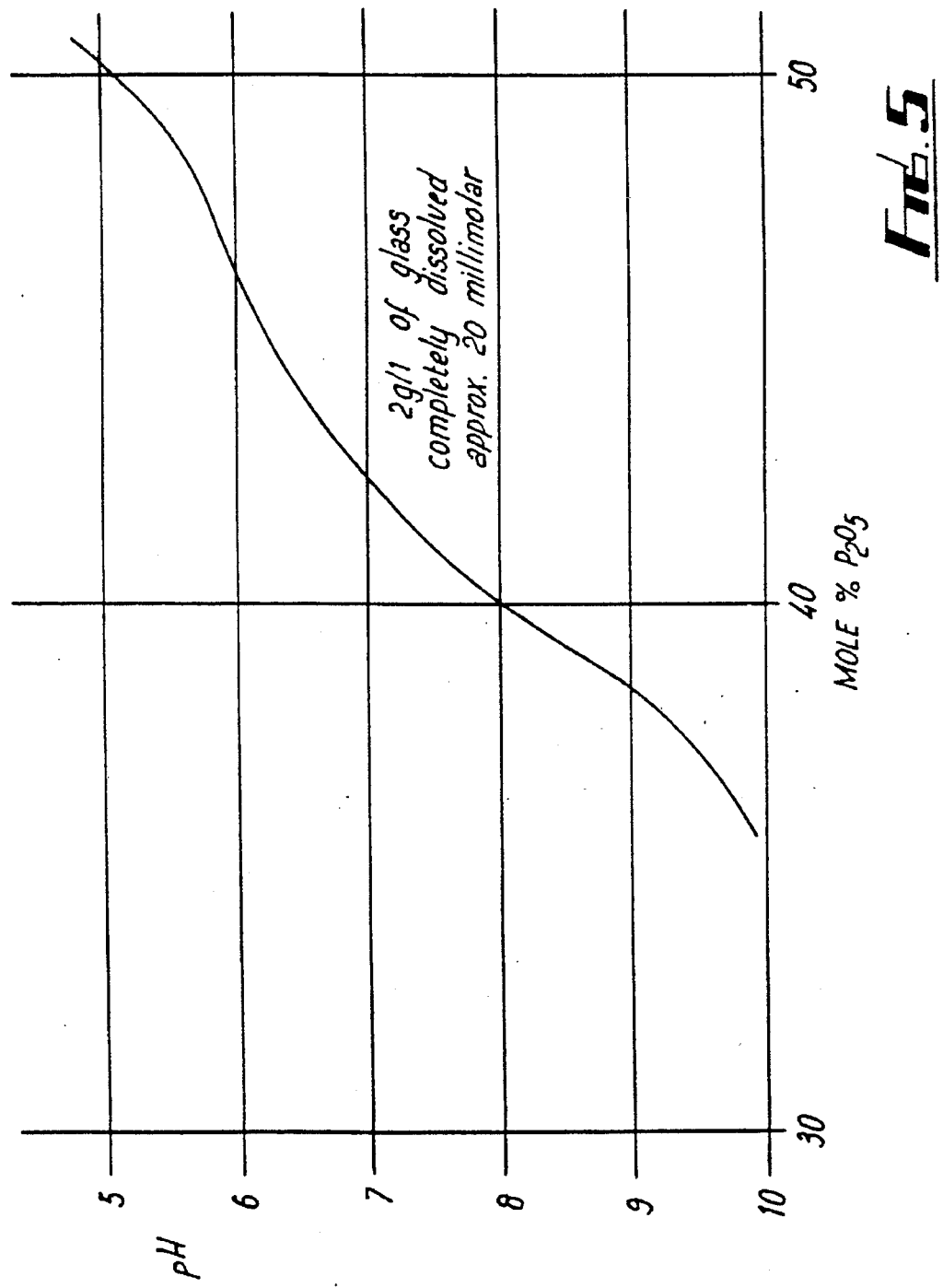

1

MEDICINAL SUBSTANCE FOR TOPICAL APPLICATION

This application is a continuation of application Ser. No. 08/121,411 filed Sep. 15, 1993, now abandoned, which is a continuation of application Ser. No. 07/688,546 filed Jun. 10, 1991, now abandoned.

This invention relates to an antimicrobial composition for use in topical applications.

The antimicrobial action of silver ions is well known as are pharmaceutical formulations containing silver salts as active principle. Perhaps the best known example of such materials is silver sulphadiazine. However, silver nitrate and silver allantoinate are also used as antimicrobials.

In addition, many wounds, especially burns, are subject to contamination by organisms such as bacteria and fungi. The use of silver as an antiseptic agent in medicine is well-known, and a variety of topical preparations based on silver salts are used in the treatment of such infected wounds eg silver nitrate and silver allantoate. However, problems associated with such compounds include pain on application, staining and skin irritations. Improved substances such as silver sulfadiazine are commonly used, but they must be removed and re-applied frequently to maintain their effect. These compounds themselves can adverse cause reactions in some patients, for example a reduction in the number of leucocytes in the local area available for fighting infection in the wound and this method of treatment also results in regular disturbance of the wound, which causes discomfort to the patient.

The use of glasses which can dissolve in water and body fluid and which are applied internally of the body are well-known. These glasses are formed from phosphorus pentoxide and may be modified to dissolve over a period of minutes, months or even years, as required. To date, such glasses have been used, in medicine, for the controlled release of a number of agents, for example, drugs, hormones and trace elements, but in each case the glass has been applied internally of the body to allow the agent to leach out into the body's circulatory system.

It is known that certain glasses, in which the usual glass former, silicon dioxide, of traditional glasses is replaced with phosphorus pentoxide as the glass former, are soluble in water and body fluids. The rate of dissolution is controlled largely by the addition of glass modifiers such as calcium and magnesium oxide. In simple terms, the greater the concentration of the modifier the slower is the rate of dissolution. The rates of dissolution which can be imparted to the glasses may range from minutes to months or even to several years. It is known to include in such compositions quantities of trace elements such as copper, cobalt and selenium which will be released from the glass as it slowly dissolves over the selected period of time.

The use of water-soluble glasses has been described for a variety of purposes in the literature. For example, UK Patent Specifications numbers 1,565,906, 2,079,152, 2,077,585 and 2,146,531 describe the gradual dissolution of the glasses as providing a means of controlled release of drugs, hormones, fungicides, insecticides, spermicides and other agents with which the glasses have been impregnated. The glasses are used for example in the form of an implant or bolus.

UK Patent Specification number 2,030,559 describes the use of selenium-impregnated water-soluble glass for providing controlled release of the selenium as a trace element into cattle and sheep, the glass being applied as a subcutaneous insert. UK Patent Specification number 2,037,735 also describes a subcutaneous implant of water-soluble glass, and in this case the glass is impregnated with copper; minor quantities of trace elements such as boron, arsenic, iodine, manganese, chromium, silver, gold and gallium may also be included.

Water-soluble glass has also been proposed for use in prosthetics, for example in UK Patent Specification number 2,099,702, and for use in anticorrosive paints, as described in UK Patent Specification number 2,062,612. Further the literature provides for the use of such glasses in the controlled release of ferrous and ferric ions into the human or animal body by ingestion or implantation of the glass (UK Patent Specification number 2,081,703), and for the use of glasses in the controlled release of ions such as lithium, sodium, potassium, caesium, rubidium, polyphosphate, calcium and aluminium to patients by inclusion of the glass in a drip feed line (UK Patent Specification number 2,057,420).

Our International Patent Application No PCT/GB 88/00701 relates to apparatus for antimicrobial use in passage of fluid to or from a living body, the apparatus comprising a conduit for insertion into the body, a reservoir for fluid and a connector member for connecting said conduit to said reservoir external of the body, wherein said connector member includes a water-soluble glass impregnated with elemental silver or a compound of silver, said water-soluble glass defining at least a part of a passageway for fluid to flow between the reservoir and the conduit.

The apparatus preferably contains the impregnated water-soluble glass at a site at which bacteria can be introduced or increased in number, and the bacteriostatic or bactericidal properties of the silver has the effect of containing or reducing the risk of infection in the body. The connector member may comprise a first portion having an end adapted for connection with said conduit and a second portion having an end adapted for connection with said reservoir, the first and second portions being releasably secured together to define a fluid passageway between the reservoir and the conduit and at least one of the first and second portions having an internal lining of said impregnated water-soluble glass. The internal lining may be retained between spaced shoulders on the first or second portion, so that when the portions are separated the lining is held in position until re-connection is made.

The connector member may be in the form of a fitting which connects together upstream and downstream tubing, each of the first and second portions of the connector being disposed at an end of the respective tubing. If it becomes necessary to disconnect the tubing remote from the patient, for example to replace a full reservoir of fluid drained from the patient with a full one, the connector can be broken and the silver reduces the danger of infection to the patient through ingress of bacteria.

The connector member may consist of or include a length of tubing, for example of plastics material, rubber or silicone rubber, in which the impregnated water-soluble glass is dispersed so that the silver is released from the tubing wall.

The reservoir may also contain impregnated water-soluble glass, especially in the case where fluid is being drained from the patient, for example in urine drainage systems. During collection of the urine in the reservoir in conventional systems bacteria multiply and there is a risk that they may migrate along the drainage tubing to the patient, thereby increasing the incidence of bacteria and producing urinary tract infection. Inclusion in the reservoir of an apertured container in which silver-impregnated water-soluble glass is disposed prevents the multiplication of bacteria in the reservoir and therefore reduces the infection risk. A preferable form of container has been found to be a flexible braided polyester sleeve closed at each end to form an elongate pouch and containing granules of the glass. This system also protects nursing staff, who are required to replace full reservoirs, and/or to drain off urine from full reservoirs, by preventing proliferation of bacteria in the urine.

The apparatus may be used for example in urine drainage systems, post-surgical drainage systems, cannula systems and renal and peritoneal dialysis systems.

There is also provided a connector member having an inlet and an outlet and having walling defining a through passageway for flow of liquid from the inlet to the outlet, at least a part of said walling being formed of water-soluble glass impregnated with elemental silver or a compound of silver.

According to one aspect of the present invention, there is provided a medicinal substance for topical application which comprises a water-soluble glass containing silver orthophosphate, and means to maintain the substance in contact with a surface of a body.

According to a second aspect of the invention there is provided a method of retarding bacterial growth at the surface of a body, comprising applying to the surface water-soluble glass silver orthophosphate, and maintaining the glass in contact with the surface.

The invention can be employed, for example, in treating wounds, catheter and tubing entry points, stoma sites and body passage entrances where bacterial growth and migration are rife.

Preferably, said glass is adapted by the use of glass modifiers to give a sustained release of silver over a set period. The means to maintain the substance in contact with the surface may be a carrier combined with the glass or could be separate from the glass. If used alone, the glass may be in the form of a powder, as granules, as fibres that can be woven into a dressing form, as a sinter which may be shaped in a particular way, or cast into the required shape eg a collar to surround the area of penetration of a catheter into the body.

When combined with a carrier the glass may be used as a filler in polymers for surface release eg in silicones, natural and synthetic rubbers and medical plastics and polymers.

Alternatively, the glass may be incorporated in the adhesive of adhesive film dressings, in lint, wool, tow and gauze dressings and as part of wound management products such as foam, hydrogels and hydrocolloids, films, gels and creams.

Combinations of these examples can also be used.

Most preferably, said glass contains not more than 40 mole % $M_2O$ or MO, not less than 10 mole % $M_2O$ or MO, and not more than 50 mole % nor less than 38 mole % phosphorus pentoxide, with the inclusion of 0.05 to 5.0 mole % silver oxide.

Said alkali metal oxide may be sodium oxide ($Na_2O$), potassium ($K_2O$) or a mixture thereof; and said alkaline earth oxide may be calcium oxide (CaO), magnesium oxide (MgO), zinc oxide (ZnO) or a mixture thereof.

The glass may also contain less than 5 mole % silicon dioxide ($SiO_2$), boric oxide ($B_2O_3$), sulphate ion ($SO_4^{2-}$), a halide ion, copper oxide (CuO) or a mixture thereof.

Typically the soluble glasses used in this invention comprise phosphorus pentoxide ($P_2O_5$) as the principal glass-former, together with any one or more glass-modifying non-toxic materials such as sodium oxide ($Na_2O$), potassium oxide ($K_2O$), magnesium oxide (MgO), zinc oxide (ZnO) and calcium oxide (CaO). The rate at which the silver-release glass dissolves in fluids is determined by the glass composition, generally by the ratio of glass-modifier to glass-former and by the relative proportions of the glass-modifiers in the glass. By suitable adjustment of the glass composition, the dissolution rates in water at 38° C. ranging from substantially zero to 25 mg/cm$^2$/hour or more can be designed. However, the most desirable dissolution rate R of the glass is between 0.01 and 2.0 mg/cm$^2$/hour. The water-soluble glass is preferably a phosphate glass, and the silver may advantageously be introduced during manufacture as silver orthophosphate ($Ag_3PO_4$). The content of silver and other constituents in the glass can vary in accordance with conditions of use and desired rates of release, the content of silver generally being up to 5 mole %. While we are following convention in describing the composition of the glass in terms of the mole % of oxides, of halides and of sulphate ions, this is not intended to imply that such chemical species are present in the glass nor that they are used for the batch for the preparation of the glass.

The optimum rate of release of silver ions into an aqueous environment may be selected by circumstances and particularly by the specific function of the released silver. The invention provides a means of delivering silver ions to an aqueous medium at a rate which will maintain a concentration of silver ions in said aqueous medium of not less than 0.01 parts per million and not greater than 10 parts per million. In some cases, the required rate of release may be such that all of the silver added to the system is released in a short period of hours or days and in other applications it may be that the total silver be released slowly at a substantially uniform rate over a period extending to months or even years. In particular cases there may be additional requirements, for example it may be desirable that no residue remains after the source of the silver ions is exhausted or, in other cases, where the silver is made available it will be desirable that any materials, other than the silver itself, which are simultaneously released should be physiologically harmless. In yet other cases, it may be necessary to ensure that the pH of the resulting solution does not fall outside defined limits.

The glass may be formed by a number of methods. It may simply be cast by conventional or centrifugal procedures, or it may be prepared via one or more stages of rod, fibre or tube drawing. Other preparation techniques include foamed glass or comminution of the glass followed by pressing and sintering into a solid body. It may be presented for example as a solid body, a powder or granules of preselected size, as flakes, or in the form of a number of hollow cylinders.

A preparation of this invention may comprise a composite material containing one or more than one water-soluble glass composition. The antimicrobial properties of the preparation of the invention are due entirely to the bacteriostatic properties of silver ions.

The antimicrobial properties of the preparation of the invention were demonstrated by placing a section of silver-containing water-soluble glass, cut from a 4 mm rod, in culture medium. Over a period of 36 hours the growth of *Pseudomonas aeruginosa* was inhibited. A similar result was obtained when the culture medium was replaced with fluids recovered after use in Continuous Ambulatory Peritoneal Dialysis (CAPD). The inhibition of bacterial growth by slow release of silver has a wide range of application in those treatments where fluid enters or leaves the body by natural processes or by routes introduced by surgical intervention.

One such example exists in CAPD where patients with renal failure receive regular exchanges of dialysis fluid introduced into the peritoneal cavity. Delivery is carried out under aseptic conditions from an individual bottle or plastic bag of sterile dialysis fluid via a resident catheter in the lower abdomen. Each time the circuit is broken there is a risk of infection both at the implant site and in the peritoneum which can lead to episodes of peritonitis and also to the required removal of the implanted catheter. The interposing of silver-release glass at the connector sites, through which liquid entering or leaving the peritoneal cavity flows, offers a barrier to bacterial invasion.

Similarly, with parenteral infusions involving individual cannulae and catheters the incorporation of an antimicrobial barrier in accordance with this invention will reduce the risk to the patient.

The antimicrobial action of silver is known. One of the most widely used silver-based pharmaceutical compositions is silver sulphadiazine which is commonly used, in the form of an ointment, for the treatment of burn wounds, (which are particularly subject to contamination by colonising organisms, especially bacteria and fungi), by topical application. In contact with the wound the silver sulphadiazine, both components possessing antibiotic properties. The compound also exhibits some degree of slow or sustained release of the silver and sulphadiazine because of its relatively low aqueous solubility which, of course, retards the dissociation necessary for release of the antibiotic action. Silver nitrate and silver allantoinate are also used.

Examples of preparations of water-soluble glasses containing silver (which are referred to below as silver release inorganic polymers (SRP)) for use with the first three aspects of the invention are given in Table 1.

TABLE 1

TABLE OF GLASS CODES GIVING COMPOSITION

| GLASS CODE | $Na_2O$ mol % | CaO mol % | $P_2O_5$ mol % | $Ag_2O$ as spec |
|---|---|---|---|---|
| D060689-1 | 28 | 20 | 50 | 2 mole % |
| D060689-2 | 28 | 22 | 50 | 0 mole % |
| D281188-1 | 36 | 14 | 50 | 0 mole % |
| D041188-1 | 35 | 14 | 50 | 1 mole % |
| D011288-1 | 35 | 14 | 50 | 1 mole % |
| D221188-1 | 30 | 19 | 50 | 1 mole % |
| D141288-1 | 30 | 20 | 50 | 0 mole % |
| D100688-1 | 22 | 25 | 50 | 10 wt % |
| D070989-1 | 26 | 23.5 | 47 | 3.5 mole % |
| D141189-1 | 27.75 | 21.75 | 47 | 3.5 mole % |
| J290487-4 | 11.63 | 37.44 | 50.00 | 10 wt % |
| J010587-2 | 12.63 | 38.44 | 50.88 | 8 wt % |

SRP compositions D060689-1 (with silver) and D060689-2 (without silver) were used to test effectiveness against organisms. Test discs of the SRP were placed on plain DST agar; one control and two test discs per plate. The plates were flooded with suspensions of test organisms, drained and dried. After incubation the widths of the zones of inhibition around the SRP discs were measured. In all cases the test samples gave significant zones of inhibition. In all cases, the controls (without silver) showed no zones of inhibition. The organisms tested were as follows: P vulgaris, P mirabilis, P rettgeri, Providence spp., Ps aeruginosa, Staph. epidermidis, NCTC, E coli, Oxford Staph., C albicans, K aerogenes, Enterococcus, Ent cloacae, MRSA, Acinetobacter, S Marcescens. The full results of this test are shown in Table 2.

TABLE 2

| | 24 hrs | | 48 hrs | |
|---|---|---|---|---|
| | Test | Control | Test | Control |
| 1. Pro vulgaris | 6.25 | 0 | 6.25 | 0 |
| | 6.25 | 0 | 6.25 | 0 |
| 2. Pro mirabilis | 6.5 | 0 | 6.5 | 0 |
| | 6.0 | 0 | 6.25 | 0 |

TABLE 2-continued

| | 24 hrs | | 48 hrs | |
|---|---|---|---|---|
| | Test | Control | Test | Control |
| 3. Pro rettgeri | 5.0 | 0 | 4.25 | 0 |
| | 4.75 | 0 | 4.25 | 0 |
| 4. Ps. aeruginosa | 6.75 | 0 | 5.75 | 0 |
| | 6.75 | 0 | 6.25 | 0 |
| 5. Providence spp | 5.75 | 0 | 3.75 | 0 |
| | 5.5 | 0 | 3.75 | 0 |
| 6. NCTC E coli | 6.75 | 0 | 6.75 | 0 |
| | 6.75 | 0 | 6.75 | 0 |
| 7. Oxford Staph | 5.75 | 0 | 5.25 | 0 |
| | 5.75 | 0 | 5.25 | 0 |
| 8. Staph eipidermidis | 6.00 | 0 | 3.75 | 0 |
| | 6.00 | 0 | 3.75 | 0 |
| 9. C albicans | 10.00 | 0 | 0 | 0 |
| | 9.00 | 0 | 0 | 0 |
| 10. K aerogenes | 4.5 | 0 | 4.0 | 0 |
| | 4.5 | 0 | 4.0 | 0 |
| 11. Enterococcus | 1.5 | 0 | 1.5 | 0 |
| | 1.75 | 0 | 1.75 | 0 |
| 12. Ent Cloacae | 3.5 | 0 | 3.25 | 0 |
| | 3.25 | 0 | 2.75 | 0 |
| 13. MRSA | 5.25 | 0 | 5.75 | 0 |
| | 5.0 | 0 | 5.75 | 0 |
| 14. Acinetobacter | 5.5 | 0 | 5.75 | 0 |
| | 5.25 | 0 | 5.75 | 0 |
| 15. S marcescens | 6.0 | 0 | 5.5 | 0 |
| | 5.5 | 0 | 5.5 | 0 |

SRP compositions D281188-1 (without silver), D041188-1 (with silver) and D011288-1 (with silver) were subjected to gamma radiation and showed no significant change in the performance of the SRP. Samples of the SRP were tested after 0, 1, 2 and 3 exposures to 25 KGy of gamma irradiation.

SRP composition D100688-1 (with silver) was used to test for skin reactions. Volunteers wore SRP impregnated patches for up to 10 days. No discomfort or irritation was reported. The SRP used in this test was composed of material to demonstrate the worst possible case.

Incorporation of SRP composition D141189-1 (with silver) into silicone rubber sheeting has been demonstrated as a viable vehicle for the delivery of effective quantities of active silver ions. Silicone rubber sheets impregnated with SRP were cut into small discs and put onto agar which was then inoculated with various organisms. Again significant zones of inhibition were recorded and the results are shown in detail in Table 3. The SRP in the silicone samples has been formulated to release active silver ions over a 3–5 day period. Any period of release can be accommodated.

TABLE 3

| | DISC | | | | | |
|---|---|---|---|---|---|---|
| ORGANISM | A30 | A15 | B30 | B15 | B10 | B5 |
| E coli | ++ | ++ | ++ | ++ | ++ | ++ |
| Klebsiella sp | ++ | ++ | ++ | ++ | ++ | ++ |
| Proteus sp | ++ | ++ | ++ | ++ | ++ | ++ |
| Ps aeruginosa | ++ | ++ | ++ | ++ | ++ | ++ |
| Staph aureus | + | + | + | + | + | − |
| Coag neg staph | + | + | ++ | + | + | − |
| MRSA | + | + | ++ | + | + | − |

Table
Zones of inhibition achieved by different silicon discs against a range of organisms (++ = complete inhibition of growth, + = partial inhibition of growth, − = inhibition of growth).

Studies have also been carried out using SRP composition D141189-1 (with silver) to assess systemic levels of silver (from blood, urine, faeces surrounding tissue and vital organs) in mice with silver releasing implants. No readable level of silver was achieved except in the local tissues, and possibly in blood and urine. Work with burns patients treated with silver sulphadiazine has shown that silver tends to remain local to its implant site showing little ability to migrate through the tissues. Sheets of silicone rubber containing 10% SRP were cut into discs approximately 10 mm in diameter and 2 mm thick. These were implanted subcutaneously into three groups of three mice. A fourth group contained three mice for control purposes into which silicone samples without SRP were implanted. Group 1 mice and one control were sacrificed on day 2, group 2 and one control on day 5 and group 3 plus one control on day 10. The samples from each group were prepared against standard solutions for analysis of silver levels by atomic absorption spectrophotometry. The implants showed only a mild local tissue reaction with silver present and no silver was detectable in the samples of vital organs.

The ability of these SRP's, when incorporated in a dressing or dispersed in a carrier, to sustain the release of active levels of silver over a period of days or even weeks, if required, offers a simple and adaptable form of treatment which may be 'tailor-made' to requirements. Thus burn sepsis, surgical and traumatic wounds and ulcers and pressure sores may be effectively treated.

Examples of the use of such SRP's are given below:

a) If the SRP powder is mixed with a filler it may be pressed into the desired shape and then heated to fuse as a sinter in its final form.

b) Sheet material may be formed by mixing a polysaccharide such as alginate with SRP granules and subjecting the mix to a paper-making process so producing a board. Paper can be incorporated to give mechanical strength. In this way a dressing or a collar can be produced.

c) The SRP may be incorporated into silicon rubber and the rubber then applied to the treatment area, for example as a pad or collar. Catheter bodies, surface linings of cannulae, drainage tubes and the like, or superficial silicon coating of various instruments and appliances may be protected by rubber containing SRP.

In such uses, the SRP-impregnated rubber may form the entire wall thickness of the catheter or other tubing, or may be used in the form of a sleeve or coating on the outer face of a conventional catheter or tube whose wall is made of PVC or other material.

A further important use of the present invention is in preventing bacteria spread and growth around punctures in the skin or around the entrance of body passages, for example the urethra. The areas around catheters which are in place for prolonged periods of time, or around stoma sites, are prone to bacterial residence and multiplication, and thus infection can arise. A collar of material used in the present invention can be applied around the catheter or stoma site in order to prevent proliferation of bacteria.

The urethra, and hence the bladder, can also become infected by migration of bacteria in the perineal region, especially as the environment in that area is conductive to bacterial growth. To combat this, a pad, towel or tampon carrying SRP may be applied to the region; and the silver ions gradually released act as a bacteriostat or bactericide controlling the incidence and spread of bacteria over a prolonged period.

The advantages derivable from the present Application include the following:

(1) sustained and controlled release of silver ions to limit bacterial incidence and spread;

(2) small quantities of silver can be used to avoid electrolyte imbalance and minimise the risk of leukopenia, and also to reduce cost;

(3) the glass is biodegradable and so disappears from the body without adverse effect;

(4) the glass is compatible with existing dressings and other topical applications;

(5) the exclusion of micro-organisms from the skin and wounds prevents their proliferation and limits their transfer from the site to ambient environment;

(6) the material used in the invention provides an environment conductive to healing; and (7) trace elements such as zinc and magnesium can be included for additional beneficial effect.

Embodiments of the fourth aspect of the present invention will now be described by way of example with reference to the accompanying drawings, in which:

BRIEF DESCRIPTION OF THE DRAWINGS

FIG. 1 is a side view of apparatus for use with the present invention;

Referring to FIG. 1, the apparatus comprises an indwelling urinary catheter 2 having inflatable balloon portions 4, 6 for maintaining the catheter in position in the urethra with the free end 8 in the bladder to collect urine through apertures 10, 12. At the outer end the catheter 2 terminates in a first portion 14 of a connector 16 whose second portion 18 leads to tubing 20 which enters a urine collection bottle 22. The bottle 22 has at its lower end remote from the tubing 20 a drain plug 24. The connection between the first and second portions 14, 18 of the connector represents a site of potential contamination by bacteria which can be introduced on releasing the connector 16, for example to change the bottle 22 and tubing 20.

Figure 2A:
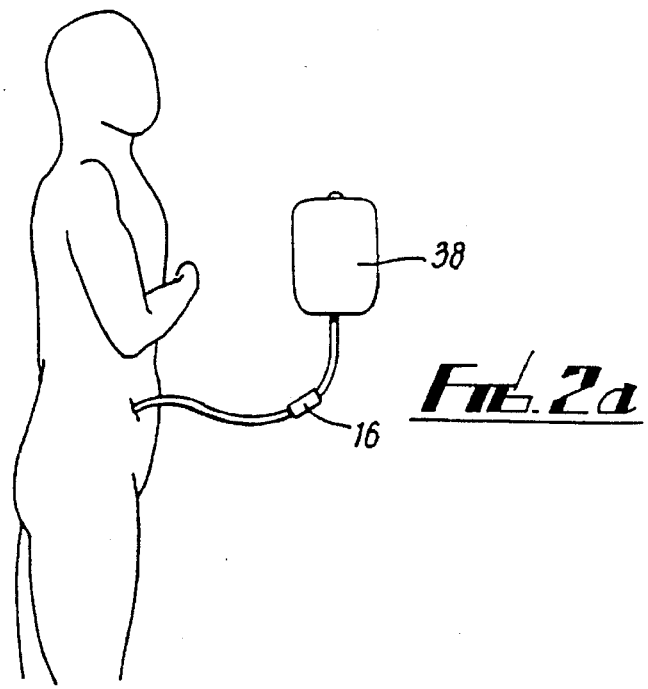
FIG. 2(a) and (b) are side views of different forms of the apparatus in use.

The urine itself is contaminated and the bacteria can reproduce in the bottle 22 as the urine collects in it. Thus when a nurse empties the bottle 22 through the drain plug 24 there is a risk of bacteria being transferred to the nurse. Further, bacteria in the bottle may find their way along the tubing 20, connector 16 and catheter 2 into the patient's bladder, causing infection.

In order to prevent such infection by bacterial reproduction and transfer, the first portion 18 of the connector 16 has a peripheral recess 26 defined by spaced shoulders 28, 30, and a sleeve or lining 32 of water-soluble glass impregnated with silver is retained in the recess 26 to form part of the flow passageway for urine through the connector. Further, the bottle 22 contains a braided pouch 34 within which are held granules of the impregnated water-soluble glass, the pouch being tubular and closed at each end. The material of the pouch 34 is such that is contains interstices which allow urine to pass through but which are small enough to prevent the granules of the glass escaping.

In use the glass sleeve 32 and the glass in the pouch 34 act as a bacteriostat preventing an increase in the number of bacteria in the urine itself and of bacteria introduced in the event of the connector 16 being opened, for example to change the bottle 22. This occurs by virtue of the gradual dissolution of the glass, releasing the silver with its bacteriostatic properties over a prolonged period. The composition of the glass determines the rate of silver release.

Figure 2B:
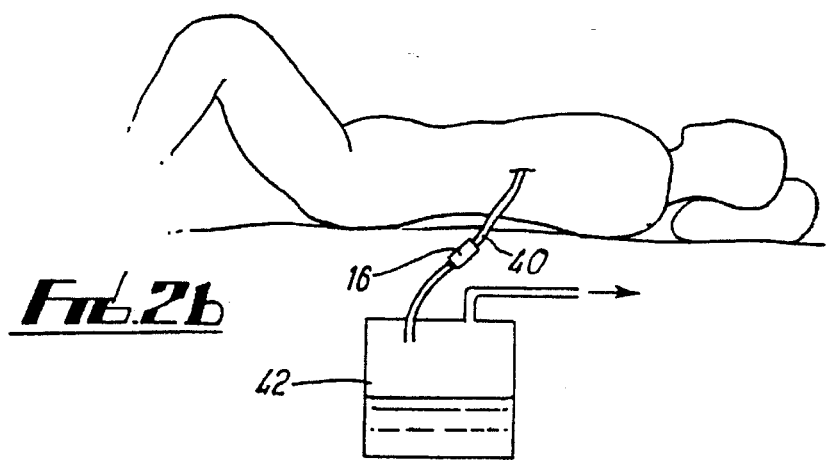

FIG. 2(a) illustrates the use of a connector 16, which is of similar construction to that shown in FIG. 1, in peritoneal dialysis in which fluid passes from a reservoir 38 into the peritoneum of the patient. In this case the fluid itself is sterile so the reservoir 38 need not contain a pouch 34 as in FIG. 1, but the sleeve 32 is required in the connector 16 to deal with bacteria which may be introduced when the connector is opened in order to replace the reservoir 38 when empty. FIG. 2(b) illustrates the apparatus in post-surgical drainage, in which suction is applied through a line 40 to the patient to draw fluid from the operation site into a collection bottle 42. Again, the connector 16 is of similar construction to that of FIG. 1 and includes the silver-impregnated sleeve 32.

Figure 3:
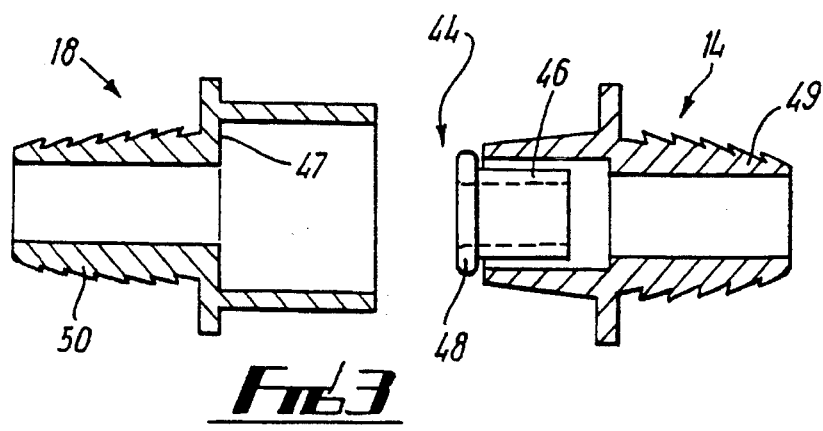
FIG. 3 is a side sectional view of an alternative connection member of this apparatus.

Referring now to FIG. 3, the connector 16 has first and second portions 14, 18 having an ingot 44 of silver-containing water-soluble glass between them. The ingot 44 is in the form of a solid sleeve 46 having an annular flange 48 at one end to bear against an end face of the second portion 18. The first and second portions 14, 18 each have a fitting 49, 50 for receiving an end portion of rubber tubing. The sleeve 46 fits within the first portion 14 so as to contact fluid passing through the connector 16.

In the connector of FIG. 3, the ingot 44 is made by mixing together 35 mole % of $NaH_2PO_4$, 15 mole % of $CaHPO_4$ and 50 mole % of $P_2O_5$, heating the mixture at 1050° C. for 20 minutes, and cooling and grinding the glass thus obtained until it forms a powder. This powder is then weighed and up to 10% by weight of silver orthophosphate ($Ag_3PO_4$) is added and mixed in. The mixture is then heated to 1050° C. to produce a homogeneous impregnated water-soluble glass, cast into shape and annealed.

The granulated form of the glass provided in the pouch 34 of FIG. 1 can also be made in this way, with a final granulation stage instead of casting.

Alternatively the silver orthophosphate can be included in the original mix to allow a single heating stage.

It has been found that if the silver-impregnated water-soluble glass used in these embodiments of the invention is heated directly at its surface after its manufacture, in a manner that creates a rapid temperature gradient through the material, elemental silver forms at the surface in a fine layer which in use provides an initial increased rate of dissolution of the silver into the fluid until the surface layer has all dissolved, after which the glass dissolves as normal with a slower rate of release of silver. In producing this effect it is important that the heating is not sustained after the formation of the silver surface layer as the glass otherwise may devitrify and the release rate of the silver becomes unpredictable.

The glass is dissolved by the breakup of the 3-D phosphorus-oxygen skeleton by the attacking $H^+$ and $OH^-$ ions and molecular $H_2O$ causing the release of phosphorus-oxygen fragments and associated cations.

| GLASS + WATER | PHOSPHATE IONS | + INCOMPLETE IONS |
|---|---|---|
| ($H^+$, $OH^-$, $H_2O$) | $(P_nO_{3n+1})^{(n+2)-}$ | eg. $(HPO_4)^{2-}$ |

The solution rate of the glass is approximately equal to the sum of the reactions of $H^+$, $OH^-$ and $H_2O$ with glass The attack by $H^+$ is the fastest, hence the solution rate, R, is a monotonic function of the hydrogen ion concentration, (except in very alkaline solutions).

The pH of solution due to the dissolution of products is dependent on the composition of the glass in the ratio $(M_2O+MO)/P_2O_5$ and in the volume and flow-rate of the aqueous solvent.

Figure 4:
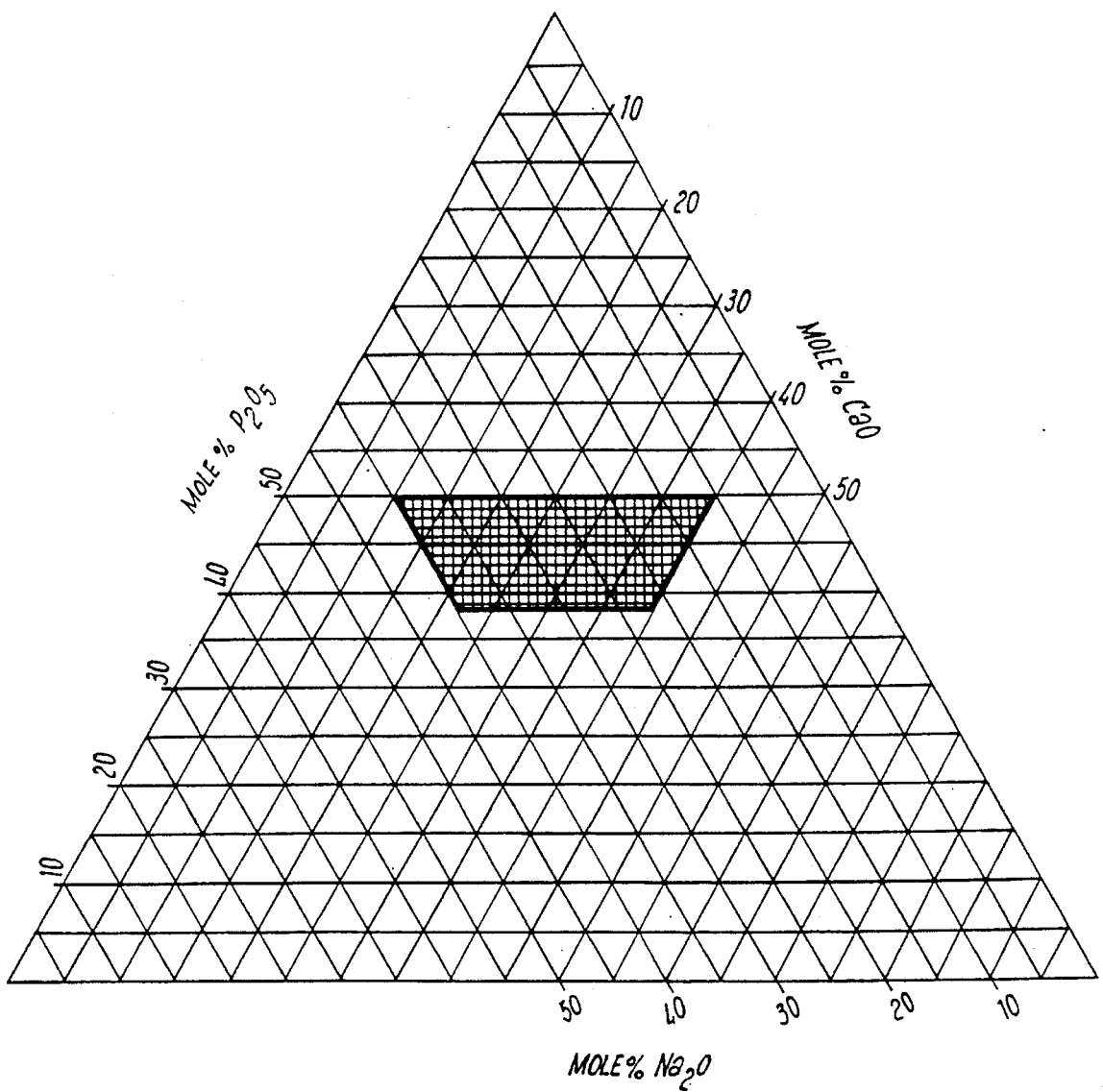
FIG. 4 is a graph of the basic glass composition of the present invention in an MO, $M_2O$ and $P_2O_5$ system; and, FIG. 5 is a graph showing the pH of solution products as a function of $P_2O_5$ content.

FIG. 4 shows a graph indicating the limits of the glass composition in the MO, $M_2O$ and $P_2O_5$ system. The shaded area describes the most desirable composition, ie. 38–50 mole % phosphorus pentoxide and 10–40 mole % $M_2O$ (eg. sodium oxide) and MO (eg. calcium oxide) assuming the inclusion of 0.05–5.0 mole % silver oxide. Adverse effects of pH on solution rate can be controlled by alteration to the basic glass composition.

FIG. 5 shows this in the form of a graph showing the pH of the solution products of 2 g/l of glasses of varying composition, which have completely dissolved (ie. a concentration of 20 mMol approximately).

It is understood that the solution rate, R, of the glass is also, to some extent, dependent on the pH of the aqueous solvent. We chose to specify the solution rate, R, as mg of glass per $cm^2$ per hour by water of pH 7.0 at 38° C. While the solution rate does not change significantly as the pH is changed from 9-4, at values of pH<4.0 the solution rate increases rapidly as the solvent becomes more acid. It will be clear that if the glass is to be used in aqueous solutions with a pH outside the range 4–8 the composition of the glass should be selected to give the required solution rate in an aqueous solvent of this particular pH.

The temperature dependence of solution rate is the temperature dependence of the chemical reaction and is of the general form: $R=R_o e^{-A/kT}$ where A is the activation energy of the solution reaction and is such that the solution rate, R, doubles for each 10° C. rise in temperature.

Experiments using the invention will now be described by way of example.

The silver-impregnated water-soluble glass was produced in two forms which would enable its incorporation into the urinary catheter collection system of FIG. 1 but using the connector shown in FIG. 3:

1. A silver-impregnated glass ingot inside a plastic connector which would be situated between the distal end of the catheter and the proximal end of the urine collection bag tubing. The reason for siting the silver glass here is that many episodes of urinary tract infection in catheterised patients are thought to result from contamination of the catheter/bag junction when the collection bag is disconnected and reconnected.
2. A porous plastic pouch containing small granules of silver-impregnated glass which would be situated inside the collection bag releasing silver ions into the collected urine. This would reduce the numbers of bacteria present in the collection bag which is thought to be a potential source of cross-infection in wards where there are several catheterised patients.

Experiment 1

Brain heart infusion broth containing small pellets of silver-impregnated glass were inoculated with small numbers of different test organisms and the broths incubated at 37° C. overnight. Test organisms used were Escherichia coli
Pseudomonas aeruginosa
Proteus mirabilis
Klebsiella sp
Staphylococcus aureus
Staphylococcus epidermidis The broths were subcultured after 48 hours to assess whether bacterial growth had been inhibited or not. Control cultures were also set up which did not contain silver-impregnated glass pellets.

Experiment 2

Pooled samples of urine containing varying numbers of bacteria ranging from $1 \times 10^5$ to $1 \times 10^7$ organisms per ml of urine were run through the silver-impregnated glass ingot containing connector at the rate of 1 ml per minute (the approximate rate at which urine flows through a urinary catheter) for 2 hours. The number of organisms present in the urine before and after flowing through the connector and after incubation of the collected urine at room temperature for 24 hours were estimated. These were compared to the numbers of organisms present in similar samples of the pooled urine which had not been passed through the connector.

Experiment 3

Filtered (sterile) urine was run through the silver-impregnated glass connector at the rate of 1 ml per minute for 2 hours as before. The connector was then artificially contaminated with $1 \times 10^6$ organisms of E. coli and sterile urine run through the connector for a further 1 hour. This was to simulate contamination of the connector for a further 1 hour. This was to simulate contamination of the connector during changing of the collection bag. The number of organisms present in the collected urine was estimated immediately after collection (Time 0) and after 24, 48, 72 and 96 hours' incubation at room temperature.

This experiment was also carried out using nutrient broth instead of sterile urine (when urine was unavailable).

Experiment 4

Sterile urine was allowed to flow through the silver-impregnated glass connector at the rate of 1 ml per minute for 24 hours. Several samples were taken during this time for silver estimation in order to gain a picture of the rate of silver release into the collected urine.

Experiment 5

Filtered (sterile) urine was collected in a container containing silver-impregnated water-soluble glass granules in a braided plastic pouch. This urine was then artificially contaminated with a known number of organisms of E. coli and the collected urine incubated at room temperature for 4 days, the numbers of organisms present in the urine being estimated daily.

Results

Preliminary experiments which assessed the ability of silver-impregnated glass to inhibit the growth of different types of bacteria showed that the glass pellets inhibited the growth of all types of bacteria except the Proteus mirabilis.

In Experiment 2, passing the urine through the connector did not immediately reduce the numbers of organisms present in the urine, but after 24 hours' incubation there was approximately a ten-fold reduction in the numbers of organisms in the urine which had been passed through the connector when compared with the control urine.

When sterile urine or nutrient broth was used and the connector artificially contaminated with E. coli, the numbers of organisms in the control urine had significantly multiplied after 24 hours' incubation, but the test urine which had been passed through the connector showed very small numbers of organisms present after 24 and 48 hours and regrowth of the E. coli did not occur until after 72 or 96 hours' incubation.

The preliminary results of the experiments assessing the use of the plastic pouch containing silver-impregnated glass granules to inhibit organism growth gave positive results.

Both the glass-containing connector and the plastic pouch containing glass granules released enough silver to inhibit the growth of bacteria and can be incorporated into urinary collection systems in order to reduce the risk of urinary tract infection in catheterised patients.

In the above Experiments the ingot contained in the connector comprised 35 mole % $NaH_2PO_4$, 15 mole % $CaHPO_4$ and 50 mole % $P_2O_5$, and 10% by weight of silver. This resulted in a rate of release of silver of 1 mg per $cm^2$ per hour.

The granules in the plastic pouch comprised 25 mole % $NaH_2PO_4$, 25 mole % $CaHPO_4$ and 50 mole % $P_2O_5$, with 5% by weight of silver. The silver release rate was 0.6mg per $cm^2$ per hour.

In general, an increase in the amount of sodium present in the glass increases the rate of dissolution and therefore of silver release when the $P_2O_5$ content remains constant.

Modifications and improvements may be incorporated without departing from the scope of the invention.

I claim:

1. A medicinal substance capable of retarding bacterial growth at a surface of a body comprising a water-soluble glass comprising phosphorus pentoxide as a glass-forming substance, said glass containing silver orthophosphate and means to maintain the substance in contact with a surface of a body.

2. A medicinal substance according to claim 1, wherein the water-soluble glass is in the form of a powder.

3. A medicinal substance according to claim 1, wherein the water-soluble glass is in the form of fibres woven into a dressing.

4. A medicinal substance according to claim 1, further comprising a polymer in which the glass is used as a filler for surface release.

5. A medicinal substance according to claim 1, wherein the water-soluble glass further comprises sodium oxide and calcium oxide.

6. A medicinal substance, according to claim 1 or claim 5, in which said silver orthophosphate is incorporated in said glass at a glass forming temperature.

7. The method of retarding bacterial growth at the surface of a body, said surface being accessed by a body fluid, said method comprising applying a water-soluble glass to the surface, said glass comprising phosphorus pentoxide as a glass-forming substance, and said glass being impregnated with silver orthophosphate as a source of silver ions and maintaining the glass in contact with the surface, so that a controlled release of an effective amount of silver ions is obtained on dissolution of the glass in said body fluid.

* * * * *